United States Patent [19]

Gluck

[11] Patent Number: 4,919,837

[45] Date of Patent: Apr. 24, 1990

[54] ANTISEPTIC CLEANSING COMPOSITION COMPRISING A WATER-SOLUBLE SALT OF CHLORHEXIDINE

[76] Inventor: Bruno A. Gluck, 20 King Avenue, Balgowlah, New South Wales 2093, Australia

[21] Appl. No.: 876,876

[22] PCT Filed: Sep. 24, 1985

[86] PCT No.: PCT/AU85/00238

§ 371 Date: May 23, 1986

§ 102(e) Date: May 23, 1986

[87] PCT Pub. No.: WO86/02090

PCT Pub. Date: Apr. 10, 1986

[30] Foreign Application Priority Data

Sep. 26, 1984 [AU] Australia .............................. PG7325

[51] Int. Cl.$^5$ ............................................... C11D 1/72
[52] U.S. Cl. ....................................... 252/106; 514/636
[58] Field of Search ......................... 252/106; 514/636

[56] References Cited

U.S. PATENT DOCUMENTS

| T943,010 | 2/1976 | Pettoruto | 424/316 |
|---|---|---|---|
| 2,830,006 | 4/1958 | Birtwell et al. | 252/106 |
| 4,420,484 | 12/1983 | Gorman et al. | 514/332 |
| 4,456,543 | 6/1984 | Owens | 252/106 |

FOREIGN PATENT DOCUMENTS

| 4274672 | 11/1973 | Australia | 252/106 |
|---|---|---|---|
| 0136231 | 4/1985 | European Pat. Off. | 252/106 |

OTHER PUBLICATIONS

Manufacturing Chemist & Aerosol News, pp. 29–33, Oct. 1973.

Merck Index, 10th Edition, p. 295, ICI Product Information on Hibitane, (1983).

*Primary Examiner*—Mary C. Lee
*Assistant Examiner*—Zinna Northington-Davis
*Attorney, Agent, or Firm*—Cushman, Darby & Cushman

[57] ABSTRACT

Antiseptic cleansing compositions and in particular to those containing a water soluble salt of chlorhexidine (N,N'-bis (4-chlorophenyl)-3,12-diimino 2,4,11,13-tetrazatetradecanediimidamide) as its active antibacterial ingredient. The present invention provides an antibacterial composition comprising from 0.1% w/v to 10.0% w/v of a water soluble salt of chlorhexidine, at least one nonionic surfactant and a diluent or carrier, wherein the weight ratio of the chlorhexidine salt to the nonionic surfactant and an inert diluent or carrier, wherein the weight ratio of the chlorhexidine salt to the nonionic surfactant is not more than 1:7.

13 Claims, No Drawings

ANTISEPTIC CLEANSING COMPOSITION COMPRISING A WATER-SOLUBLE SALT OF CHLORHEXIDINE

TECHNICAL FIELD

The invention relates to antiseptic cleansing compositions and in particular to those containing a water soluble salt of chlorhexidine [N,N''-bis(4-chlorophenyl)-3,12-diimino-2,4,11,13-tetraazatetradecanediimidamide] as its active antibacterial ingredient.

BACKGROUND ART

The transmission of pathogenic microorganisms by hands in medical practice has long been recognized as a source of infection in the treatment of patients and in surgery. Physical barriers such as surgical gloves often prove insufficient protection because of the high incidence of punctures and minor cuts by surgical instruments.

Following the usual scrub-up procedure, the application of antiseptic fluids to the hands of operating theatre staff prior to surgery is common practice to reduce viable organisms on the skin to a minimum.

It would therefore be a great advantage to combine washing and disinfectant action in one single operation. Most suitable for a combined head washing and degerming product would be an antibacterial agent which combines a broad antibacterial spectrum, covering the whole range of Gram positive and negative bacteria, with continuous residual bactericidal activity after application, and low irritation to the skin. Chlorhexidine has such properties and is available in water soluble forms such as the gluconate and acetate salts.

A disadvantage of the chlorhexidine antibacterial agents is that through their cationic character they are incompatible with anionic surfactants. Combination with cationic surfactants for hand washing is not advisable as the high concentration of the cationic surfactant necessary for good detergency could give rise to skin irritation. Amphoteric surfactants, due to their anionic and cationic character, depending upon pH are equally unsuitable for the reasons given above. It was further found that chlorhexidine in combination with nonionic surfactants suffers considerable losses in antibacterial activity.

Australian Patent 459,343 describes a skin cleansing composition containing salts of chlorhexidine in combination with a polyoxyethylene-polyoxypropylene block copolymer. The block copolymer is a low-foaming nonionic surfactant, and high proportions of as much as 20-25% of such copolymers are necessary to give sufficient sudsing expected from that type of product, even when foam boosters such as an alkyl amine oxide is incorporated in the composition.

The compositions exemplified in Australian Patent 459,343 contain 4% w/v chlorhexidine which is well above the amount which normally would be required for skin disinfection. This is due to the fact that at the high concentration of nonionic surfactant, considerable deactivation takes place leaving only a small amount of the chlorhexidine available for antibacterial activity.

It is well known that nonionic surfactants have an adverse effect on the skin, through defatting which increases with higher concentration especially on sensitive skin. High concentrations of chlorhexidine have an irritating effect on the skin. Reduction of the concentration of chlorhexidine and nonionic surfactants in a nonionic surfactant system, while still retaining sufficient available chlorhexidine for the desired antibacterial effectiveness, would not only effectively reduce the risk of skin irritation on repeated application, but also reduce costs of such compositions by a considerable degree.

DISCLOSURE OF INVENTION

The hand & skin cleansing compositions of the invention have the following advantages:

1. less deactivation of the chlorhexidine in the presence of a surfactant, therefore higher antibacterial activity and more effective disinfectant-cleansing compositions, 2. lower amounts of chlorhexidine, therefore less risk of irritation of sensitive skin, 3. lower quantities of nonionic surfactants, therefore less adverse effect on the skin because of decreased defatting action of the surfactants, and 4. lower quantities of chlorhexidine and surfactants reduce costs considerably.

These advantages of the new composition do in fact allow the extension of their use from antiseptic hand and skin cleansing products to low cost compositions for the disinfection and cleansing of surgical instruments and inanimate surfaces in general.

The present invention therefore provides an antibacterial composition comprising a water-soluble salt of chlorhexidine, a nonionic surfactant and an inert diluent or carrier, wherein the nonionic surfactant is at least one compound having the formula R—O—(—CH$_2$CH$_2$O—)$_n$H, wherein R is the residue of an alkylphenol or a fatty alcohol and n is a number sufficiently high to assure water solubility between ambient temperatures and 45° C., the chlorhexidine salt being present at a concentration of from 0.1 to 10.0% w/v and the nonionic surfactant being present at a concentration of not greater than 25% w/v, wherein the weight ratio of the chlorhexidine salt to the nonionic surfactant is not greater than 1:7, with the proviso that the composition does not contain a polyoxyethylenepolyoxypropylene condensate or an amphoteric surfactant.

The compositions of the invention find application as cleansers for animate or inanimate objects and surfaces. They can be used for cleansing and sterilizing surgical and other instruments and as bath or shower additives or liquid antiseptic soaps. Suitable concentrations of water soluble chlorhexidine salt, for skin cleansers are from 1% to 4% w/v, preferred concentrations being 2% and 4% w/v; and for surface cleansers are up to 1% w/v. The compositions of the invention can if so desired be manufactured as concentrates containing 5 to 10% v/v of chlorhexidine for subsequent dilution. Any water soluble chlorhexidine salts are suitable in the compositions of the invention, however, those having a water solubility of not less than 0.5% w/v at ambient temperatures are preferred. Examples of such suitable salts are the gluconate, isethionate, formate, acetate, glutamate, succinamate, mono-diglycollate, dimethanesulfonate, lactate, di-isobutyrate and the glucoheptonate. The preferred salts are the gluconate and the acetate.

The optimum amount of chlorhexidine and the optimum ratio of chlorhexidine to surfactant will depend upon the surfactant chosen and can readily be determined within the specified limits experimentally.

The nonionic surfactant chosen will depend on the intended application of the composition and may be selected from for example alkyl-, aryl-, fatty acid-, and alcohol-polyethoxylates, polyalkylene copolymers such as derived from ethylene oxide and propylene oxide.

The preferred nonionic surfactants are those of general formula:

$$R-O-(-CH_2CH_2O-)_nOH$$

wherein R is the residue of an alkylphenol, a fatty alcohol or a fatty acid, and n is a number sufficiently high to assure water solubility between ambient temperatures and 45° C., and where R is a nonylphenoxy-residue and containing 8.5 to 15 moles of ethoxyethylene per molecule. These are preferred for animate objects and surfaces.

When polyoxyethylenepolyoxypropylene condensates are employed as nonionic surfactants, they are not to exceed 10% w/v of the compositions. These are preferred for inanimate objects and surfaces.

Other preferred nonionic surfactants are the ethoxylates of fatty alcohols with a chain of 12 to 15 carbon atoms and an ethoxylate content of not less than 5 moles.

For skin and hand cleansers, suitable polyoxyethylenepolyoxypropylene surfactants are those where a 1% aqueous solution at a temperature of 20° C. produces a foam height of at least 70 mm according to the Ross Miles Test. Most preferred are those which produce a foam height of around 110 mm. Lower foam is desirable for surface disinfectant cleansers.

If it is desired to boots the activity of the compositions of the invention against Gram negative bacteria, suitable amounts of disinfectants active against Gram negative bacteria, an antibacterial quaternary ammonium compounds can be added.

Suitable inert diluents or carriers include water, the lower alkanols, such as ethanol or propanol, and mixtures of two or more thereof.

If increased foaming characteristics are desired in the compositions of the invention, especially in hand washing compositions, foam stabilizers and boosting agents such as the higher alkymono- or diethanolamides or alkyldimethylamino oxides can be included in the compositions of the invention.

Such suitable agents are, for example, the lauryl or cocodiethanolamide or monoethanolamide condensates or the lauryl or cetyl dimethylamine oxides. Suitable quantities range from 2.0 to 4.0% by weight of the total volume, but their use is not restricted to such quantities depending on the concentration of the chlorhexidine salt and type of nonionic surfactant contained in the composition as such agents usually have some deactivating action on the antibacterial efficiency of the chlorhexidine salt.

It will thus be necessary to check the effect of such agents on the antibacterial activity of the composition, and if necessary, adjust the quantity of foaming agent or chlorhexidine accordingly.

If it is desired to increase the stability of the compositions of the invention for shelf-life and temperature variation encountered in normal storage conditions, a small amount of an alcohol such as ethanol or isopropanol can be added. Suitable quantities in the order of 3 to 5% v/v.

For optimal bactericidal efficiency, the pH of the final composition should be between 5 and 7, and preferably about 6.5. Any acid compatible with the components of the composition can be used to adjust the pH. Acetic acid is suitable in most cases. pH greater than 8 should be avoided to prevent precipitation of the chlorhexidine free base.

The compositions of the invention may contain further conventional additives such as colouring agents and fragrances. Suitable dyes are for example, carmosine (C.I. Food Red 3), Blue E G (C.I. Food Blue 2) and tartrazine (C.I. Food Yellow 4), or mixtures thereof. Preferably, the dyes are prepared as concentrates and added to the prepared composition. Other optional ingredients include preservatives, antioxidants, emollients and thickeners compatible with chlorhexidine.

MODES FOR CARRYING OUT THE INVENTION

The following examples illustrate preferred embodiments of the present invention. They should not be construed as limiting the claims hereto.

EXAMPLE 1

Surgical Scrub-Up and Hand and Skin Cleanser

| | |
|---|---|
| Chlorhexidine digluconate 20% w/v | 10.0 mL |
| Nonylphenolethoxylate | 6.0 g |
| Cocodiethanolamide | 2.0 g |
| Glycerol | 5.0 mL |
| Isopropanol | 3.0 mL |
| Carmosine | 0.003 g |
| Water (pure), to make | 100.0 mL |

The chlorhexidine gluconate is added to a quantity of water with stirring followed by the nonylphenolethoxylate until all has been dissolved. The cocodiethanolamide is added and the pH adjusted to 6.5 with 5M acetic acid followed by the glycerol. Carmosine dissolved in water is then added followed by a fragrance dissolved in isopropanol. The volume was made up to 100 ml with water. This formulation is suitable for hospital ward and general use.

EXAMPLE 2

Antiseptic Surgical Scrub and Hand Cleanser

| | |
|---|---|
| Chlorhexidine digluconate 20% w/v | 20.0 mL |
| Nonylphenolethoxylate | 10.0 g |
| Cocodiethanolamide | 2.0 g |
| Laurylaminooxide | 2.0 g |
| Ethanol | 5.0 mL |
| Carmosine | 0.003 g |
| Water to make | 100.0 mL |

The components were mixed as in Example 1. This product is intended for operating theatre, infectious ward and intensive care ward use.

EXAMPLES 3 AND 4

Procedure of Examples 1 and 2 was repeated with the inclusion of 0.5 and 1.0% w/v of hydroxyethylcellulose respectively.

EXAMPLE 5

Antiseptic Skin Cleanser

| | |
|---|---|
| Chlorhexidine digluconate 20% w/v | 10.0 mL |
| Polyoxyethylenepolyoxypropylene glycol | 6.0 mL |
| Ethanol | 3.0 mL |

-continued

| | |
|---|---|
| Food Blue 2 | 0.003 g |
| Water to make | 100.0 mL |

EXAMPLE 6

Solution for Disinfection and Cleansing of Surgical Instruments and Equipment

| | |
|---|---|
| Chlorhexidine acetate | 0.50 g |
| Polyoxyethylenepolyoxypropylene glycol | 0.75 g |
| Permicol Green | 0.003 g |
| Water to make | 100.0 mL |

The product is prepared by adding the ingredients to the water and mixing.

EXAMPLE 7

Hospital Grade Disinfectant Cleaner

| | |
|---|---|
| Chlorhexidine digluconate 20% w/v | 0.75 mL |
| Polyoxyethylenepolyoxypropylene glycol | 0.5 g |
| Benzalkonium chloride | 1.50 g |
| Tartrazine | 0.0015 g |
| Carmosine | 0.0015 g |
| Water to make | 100.0 mL |

This product combines excellent disinfecting properties with exceptional cleansing power.

EXAMPLE 8

Disinfectant Concentrate

| | |
|---|---|
| Chlorhexidine digluconate 20% w/v | 50.0 mL |
| Polyoxyethylenepolyoxypropylene glycol | 30.0 mL |
| Ethanol | 15.0 mL |
| Food Blue 2 | 0.15 g |
| Water to make | 100.0 mL |

The concentrate is suitable for use at a dilution of 1:5 as a general disinfectant.

I claim:

1. An antibacterial composition comprising a water-soluble salt of chlorhexidine, a nonionic surfactant and an inert diluent or carrier wherein the nonionic surfactant is at least one compound having the formula $$R-O-(-CH_2CH_2O-)_nH$$

wherein R is the residue of an alkylphenol or a fatty alcohol and n is a number sufficiently high to assure water solubility between ambient temperatures and 45° C., the chlorhexidine salt being present at a concentration of from 0.1 to 10.0% w/v and the nonionic surfactant being present at a concentration of not greater than 25% w/v wherein the weight ratio of the chlorhexidine salt to the nonionic surfactant is not more than 1:7, and the composition does not contain a polyoxyethylene-polyoxypropylene condensate or an amphoteric surfactant.

2. A composition as defined in claim 1, wherein the content of nonionic surfactant does not exceed 25% w/v.

3. A composition as defined in claim 1, wherein the salt of chlorhexidine is the gluconate, isethionate, formate, acetate, glutamate, succinamate, mono-diglycollate, dimethanesulfonate, lactate, di-isobutyrate or the glucoheptonate.

4. A composition as defined in claim 3, wherein the salt is the gluconate or the acetate.

5. A composition as defined in claim 1, wherein the salt of chlorhexidine is present in a concentration of 2.0% w/v.

6. A composition as defined in claim 1, wherein the salt of chlorhexidine is present in a concentration of 4.0% w/v.

7. A composition as defined in claim 1, having a pH between 4.5 and 7.5.

8. A composition as defined in claim 1, wherein the inert diluent or carrier is water, a lower alkanol, or a mixture of two or more thereof.

9. A composition as defined in claim 1, further comprising an antibacterial quaternary ammonium compound.

10. A composition as defined in claim 1, further comprising a foaming agent.

11. A composition as defined in claim 10, wherein the foaming agent is an alkylmono- or diethanolamide, or a mono- or dialkylaminooxide or a mixture of two or more thereof.

12. A composition as defined in claim 1, further comprising a perfume, a coloring agent, a preservative, an antioxidant, an emollient or a thickener.

13. A composition as defined in claim 1, wherein the weight ratio is not more than 1:5.

* * * * *